US012704509B2

(12) United States Patent
Koser

(10) Patent No.: US 12,704,509 B2
(45) Date of Patent: Aug. 11, 2026

(54) SYSTEMS AND METHODS FOR BEAD-BASED ASSAYS IN FERROFLUIDS

(71) Applicant: Ancera, Inc., Branford, CT (US)

(72) Inventor: Hur Koser, Wallingford, CT (US)

(73) Assignee: ANCERA INC., Branford, CT (US)

( * ) Notice: Subject to any disclaimer, the term of this patent is extended or adjusted under 35 U.S.C. 154(b) by 1072 days.

(21) Appl. No.: 17/554,956

(22) Filed: Dec. 17, 2021

(65) Prior Publication Data

US 2022/0107311 A1 Apr. 7, 2022

Related U.S. Application Data

(60) Continuation of application No. 15/623,134, filed on Jun. 14, 2017, now Pat. No. 11,204,350, which is a division of application No. 14/777,512, filed as application No. PCT/US2014/030584 on Mar. 17, 2014, now abandoned.

(60) Provisional application No. 61/798,087, filed on Mar. 15, 2013.

(51) Int. Cl.

| | |
|---|---|
| ***B01L 3/00*** | (2006.01) |
| ***B03C 1/01*** | (2006.01) |
| ***B03C 1/28*** | (2006.01) |
| ***B03C 1/32*** | (2006.01) |
| ***G01N 15/14*** | (2006.01) |
| ***G01N 15/1404*** | (2024.01) |
| ***G01N 33/543*** | (2006.01) |
| *G01N 15/149* | (2024.01) |
| *G01N 27/447* | (2006.01) |
| *G01N 35/00* | (2006.01) |

(52) U.S. Cl.

CPC .... *G01N 33/54366* (2013.01); *B01L 3/50273* (2013.01); *B01L 3/502753* (2013.01); *B01L 3/502761* (2013.01); *B03C 1/01* (2013.01); *B03C 1/288* (2013.01); *B03C 1/32* (2013.01); *G01N 15/1404* (2013.01); *G01N 15/1459* (2013.01); *G01N 15/1484* (2013.01); *G01N 33/54313* (2013.01); *B01L 2200/0647* (2013.01); *B01L 2300/06* (2013.01); *B01L 2300/0654* (2013.01); *B01L 2400/043* (2013.01); *B03C 2201/18* (2013.01); *B03C 2201/20* (2013.01); *B03C 2201/26* (2013.01); *G01N 2015/1415* (2013.01); *G01N 2015/1486* (2013.01); *G01N 15/149* (2024.01); *G01N 27/44786* (2013.01); *G01N 35/0098* (2013.01)

(58) Field of Classification Search

None

See application file for complete search history.

(56) References Cited

U.S. PATENT DOCUMENTS

| | | | |
|---|---|---|---|
| 3,202,576 | A | 8/1965 | Rogers et al. |
| 3,477,948 | A | 11/1969 | Inoue et al. |
| 3,764,540 | A | 10/1973 | Khalafalla et al. |
| 3,898,156 | A | 8/1975 | Kaiser et al. |
| 4,448,534 | A | 5/1984 | Wertz et al. |
| 4,935,147 | A | 6/1990 | Ullman et al. |
| 5,076,950 | A | 12/1991 | Ullman et al. |
| 5,194,133 | A | 3/1993 | Clark et al. |
| 5,439,586 | A | 8/1995 | Richards et al. |
| 5,932,100 | A | 8/1999 | Yager et al. |
| 5,998,224 | A | 12/1999 | Rohr et al. |
| 6,038,104 | A | 3/2000 | Sato et al. |
| 6,045,755 | A | 4/2000 | Lebl et al. |
| 6,303,389 | B1 | 10/2001 | Levin et al. |
| 6,309,889 | B1 | 10/2001 | Cutler et al. |
| 6,432,630 | B1 | 8/2002 | Blankenstein |
| 6,596,143 | B1 | 7/2003 | Wang et al. |

(Continued)

FOREIGN PATENT DOCUMENTS

| | | | |
|---|---|---|---|
| CN | 101087655 | A | 12/2007 |
| CN | 201125246 | Y | 10/2008 |

(Continued)

OTHER PUBLICATIONS

Applegate et al., "Optical trapping, manipulation, and sorting of cells and colloids in microfluidic systems with diode laser bars", Optical Express 12: 4390-4398 (2004).

(Continued)

*Primary Examiner* — Christopher M Gross

(74) *Attorney, Agent, or Firm* — Myers Bigel, P.A.

(57) ABSTRACT

Some embodiments of the present disclosure are directed to systems and methods for separating, directing, and/or extracting a target molecule from a mix of molecules and may comprise a plurality of non-magnetic beads suspended in a ferro fluid, where the non-magnetic beads may be functionalized with at least one predetermined first molecule configured to bind with a target particle. A microfluidic device may be included which may comprise at least one microfluidic channel, the device configured to dynamically and/or statically receive an amount of the mix. Magnetic field means may be included and may be configured to apply a magnetic field to at least a portion of the at least one channel to exert an indirect force on the non-magnetic heads in the ferro fluid mix, and separate the non-magnetic beads from the ferrofluid. The beads may then be directed to at least one receptor region. At least one outlet may be provided which is arranged to be in communication with the at least one microfluidic channel, the at least one outlet may be configured to receive and extract the separated non-magnetic beads from the ferrofluid.

12 Claims, 1 Drawing Sheet

(56) References Cited

U.S. PATENT DOCUMENTS 6,610,186 B1 8/2003 Mayer et al.
6,620,627 B1 9/2003 Liberti et al.
6,663,757 B1 12/2003 Fuhr et al.
7,960,311 B2 6/2011 Carlson
8,364,409 B2 1/2013 Rieder et al.
8,961,878 B2 2/2015 Koser
8,961,898 B2 2/2015 Nisisako et al.
9,352,317 B2 5/2016 Koser
9,415,398 B2 8/2016 Yellen et al.
9,557,326 B2 1/2017 Inaba et al.
9,726,592 B2 8/2017 Koser
9,999,855 B2 6/2018 Koser
10,302,634 B2 5/2019 Koser
10,632,463 B2 4/2020 Koser
10,782,223 B2 9/2020 Koser
11,204,350 B2 * 12/2021 Koser .............. G01N 33/54313
11,285,490 B2 3/2022 Koser
11,383,247 B2 7/2022 Koser
2002/0003001 A1 1/2002 Weigl et al.
2002/0016751 A1 2/2002 Sekiya
2002/0049782 A1 4/2002 Herzenberg et al.
2002/0059132 A1 5/2002 Quay et al.
2002/0106314 A1 8/2002 Pelrine et al.
2002/0144934 A1 10/2002 Exner
2003/0159999 A1 8/2003 Oakey et al.
2003/0203507 A1 10/2003 Liberti et al.
2003/0235504 A1 12/2003 Lemoff et al.
2004/0018611 A1 1/2004 Ward et al.
2004/0067167 A1 4/2004 Zhang et al.
2004/0096977 A1 5/2004 Rakestraw et al.
2005/0012579 A1 1/2005 Underwood et al.
2005/0199550 A1 9/2005 Haney et al.
2005/0233472 A1 10/2005 Kao et al.
2005/0237528 A1 10/2005 Oldham et al.
2005/0244932 A1 11/2005 Harding
2005/0266433 A1 12/2005 Kapur et al.
2005/0280811 A1 12/2005 Sandell
2006/0011305 A1 1/2006 Sandell et al.
2006/0011552 A1 1/2006 Utsunomiya
2006/0013984 A1 1/2006 Sandell et al.
2006/0024690 A1 2/2006 Kao et al.
2006/0024831 A1 2/2006 Kao et al.
2006/0029948 A1 2/2006 Lim et al.
2006/0166357 A1 7/2006 Takayama et al.
2006/0188399 A1 8/2006 Smid
2006/0286549 A1 12/2006 Sohn et al.
2007/0014694 A1 1/2007 Beard et al.
2007/0015289 A1 1/2007 Kao et al.
2007/0125971 A1 6/2007 Wimberger-Friedl et al.
2007/0134809 A1 6/2007 Cho et al.
2007/0196820 A1 8/2007 Kapur et al.
2007/0215553 A1 9/2007 Yellen et al.
2007/0224084 A1 9/2007 Holmes et al.
2008/0000892 A1 1/2008 Hirano et al.
2008/0006202 A1 1/2008 Hirano et al.
2008/0035541 A1 2/2008 Franzreb et al.
2008/0038725 A1 2/2008 Luo et al.
2008/0148821 A1 6/2008 Donsky et al.
2008/0210560 A1 9/2008 Barringer
2008/0255006 A1 10/2008 Wang et al.
2008/0302732 A1 12/2008 Soh et al.
2009/0035838 A1 2/2009 Quake et al.
2009/0050569 A1 2/2009 Jung et al.
2009/0078614 A1 3/2009 Varghese et al.
2009/0148933 A1 6/2009 Battrell et al.
2009/0165876 A1 7/2009 Atkin et al.
2009/0175797 A1 7/2009 Warren et al.
2009/0220932 A1 9/2009 Ingber et al.
2009/0227044 A1 9/2009 Dosev et al.
2009/0251136 A1 10/2009 Prins et al.
2009/0325276 A1 12/2009 Battrell et al.
2010/0068824 A1 3/2010 Kimura
2010/0075340 A1 3/2010 Javanmard et al.
2010/0093052 A1 4/2010 Chalmers et al.
2010/0120077 A1 5/2010 Daridon
2011/0003392 A1 1/2011 Stayton et al.
2011/0020459 A1 1/2011 Achrol et al.
2011/0059468 A1 3/2011 Earhart et al.
2011/0065209 A1 3/2011 Heil et al.
2011/0114490 A1 5/2011 Pamula et al.
2011/0124116 A1 5/2011 Wohlstadter et al.
2011/0137018 A1 6/2011 Chang-Yen et al.
2011/0212440 A1 9/2011 Viovy et al.
2011/0262893 A1 10/2011 Dryga et al.
2011/0312518 A1 12/2011 Davis et al.
2012/0080360 A1 4/2012 Stone et al.
2012/0108470 A1 5/2012 Oh et al.
2012/0178645 A1 7/2012 Foekens et al.
2012/0190589 A1 7/2012 Anderson et al.
2012/0237997 A1 9/2012 Koser
2013/0140241 A1 6/2013 Yellen et al.
2013/0189794 A1 7/2013 Emeric et al.
2013/0261010 A1 10/2013 Bailey et al.
2013/0313113 A1 11/2013 Koser
2014/0044600 A1 2/2014 Mcalister
2014/0214583 A1 7/2014 Assuncao et al.
2014/0283945 A1 9/2014 Jones et al.
2015/0041396 A1 2/2015 Kelly et al.
2015/0151299 A1 6/2015 Koser
2016/0016171 A1 1/2016 Goel
2016/0188399 A1 6/2016 Benedict
2016/0263574 A1 9/2016 Smith et al.
2016/0266026 A1 9/2016 Koser
2016/0296944 A1 10/2016 Koser
2016/0296945 A1 10/2016 Koser
2016/0299052 A1 10/2016 Koser
2016/0299126 A1 10/2016 Koser
2016/0299132 A1 10/2016 Koser
2017/0122851 A1 5/2017 Thatcher et al.
2017/0259265 A1 9/2017 Diller et al.
2017/0285060 A1 10/2017 Koser
2017/0297028 A1 10/2017 Jones et al.
2018/0017557 A1 1/2018 Fritz et al.
2018/0029033 A1 2/2018 Koser et al.
2018/0029035 A1 2/2018 Koser et al.
2018/0128671 A1 5/2018 Paur et al.
2018/0128729 A1 5/2018 Koser
2018/0188246 A1 7/2018 Koser
2018/0361397 A1 12/2018 Koser
2019/0091699 A1 3/2019 Koser
2019/0118190 A1 4/2019 Koser
2019/0120822 A1 4/2019 Koser
2019/0339262 A1 11/2019 Koser
2020/0306758 A1 10/2020 Dhlakama
2020/0353466 A1 11/2020 Koser
2022/0212201 A1 7/2022 Koser

FOREIGN PATENT DOCUMENTS

CN 104535783 A 4/2015
CN 105142789 A 12/2015
JP 2006187770 A 7/2006
JP 2009511001 A 3/2009
JP 2009133818 A 6/2009
WO WO-9101381 A1 2/1991
WO WO-2006004558 A1 1/2006
WO WO-2006067715 A2 6/2006
WO WO-2008042003 A2 4/2008
WO WO-2008130977 A2 10/2008
WO WO-2010117428 A1 10/2010
WO WO-2010117458 A1 10/2010
WO WO-2011071812 A2 6/2011
WO WO-2011071912 A1 6/2011
WO WO-2011139233 A1 11/2011
WO WO-2012057878 A1 5/2012
WO WO-2012142664 A1 10/2012
WO WO-2013054311 A1 4/2013
WO WO-2013155525 A1 10/2013
WO WO-2014044810 A1 3/2014
WO WO-2014065317 A1 5/2014
WO WO-2014100456 A1 6/2014
WO WO-2014144340 A1 9/2014
WO WO-2014144782 A2 9/2014
WO WO-2014144810 A1 9/2014

(56) References Cited

FOREIGN PATENT DOCUMENTS

| | | |
|---|---|---|
| WO | WO-2014145765 A1 | 9/2014 |
| WO | WO-2014165317 A1 | 10/2014 |
| WO | WO-2016210348 A2 | 12/2016 |
| WO | WO-2017004595 A1 | 1/2017 |
| WO | WO-2017085098 A1 | 5/2017 |
| WO | WO-2017192633 A1 | 11/2017 |
| WO | WO-2018026605 A1 | 2/2018 |
| WO | WO-2019103741 A1 | 5/2019 |
| WO | WO-2019117877 A1 | 6/2019 |
| WO | WO-2022015845 A2 | 1/2022 |
| WO | WO-2022169905 A1 | 8/2022 |

OTHER PUBLICATIONS

Ashkin et al., "Optical trapping and manipulation of single cells using infrared laser beams", Nature 330: 769-771 (1987).

Ashkin et al., "Optical trapping and manipulation of viruses and bacteria", Science 235: 1517-1520 (1987).

Asmatulu, R. et al., "A Ferrofluid Guided System for the Rapid Separation of the Non-Magnetic Particles in a Microfluidic Device", Journal of Neuroscience and Nanotechnology, 10: 1-5 (2010).

Bautista et al., "Comparative study of ferrofluids based on dextran-coated iron oxide and metal nanoparticles for contrast agents in magnetic resonance imaging," Nanotechnology 15: S154-S159 (2004).

Beyor et al., "Immunomagnetic bead-based cell concentration microdevice for dilute pathogen detection", Biomed Microdevices 10: 909-917 (2008).

Blattner et al., "The complete genome sequence of *Escherichia coli* K-12", Science 277: 1453-1474 (1997).

Bushkin, G.G., et al., "Evidence for a Structural Role for Acid-fast Lipids in Oocyst Walls of Cryptosporidium, Toxoplasma, and Eimeria", MBIO, Nov. 1, 2013, vol. 4(5), 8 pages.

Cabrera et al., "Continuous concentration of bacteria in a microfluidic flow cell using electrokinetic techniques", Electrophoresis 22:355-362 (2001).

Castagiuolo et al., "Engineered *E. coli* delivers therapeutic genes to the colonic mucosa", Gene Therapy 12:1070-1078 (2005).

Cheong et al., "Gold nanoparticles for one step DNA extraction and real-time PCR of pathogens in a single chamber", Lab Chip 8: 810-813 (2008).

Chiou et al., "Massively parallel manipulation of single cells and microparticles using optical images", Nature 436: 370-372 (2005).

Davis et al., "Deterministic hydrodynamics: Taking blood apart", Proc Natl Acad Sci USA 103: 14779-14784 (2006).

Dittrich et al., "Lab-on-a-chip: microfluidics in drug discovery", Nat. Rev. Drug Discovery 5: 210-218 (2006).

Dufresne et al., "Optical tweezer arrays and optical substrates created with diffractive optics", Rev Sci Instrum 69: 1974-1977 (1998).

Dumesny et al., "Synthesis, expression and biological activity of the prohormone for gastrin releasing peptide", Endocrinology 147(1): 502-509 (2006).

Examination Report dated Oct. 1, 2021 for European Application No. 17837424.5, 6 pages.

Examination Report No. 1 dated Nov. 18, 2016 for Australian Application No. 2015268583, 4 pages.

Extended European Search Report dated Dec. 11, 2017 for European Application No. 10836542.0, 10 pages.

Extended European Search Report dated Dec. 13, 2017 for European Application No. 11836778.8, 9 pages.

Extended European Search Report dated Jun. 14, 2021 for European Application No. 17934894.1, 6 pages.

Extended European Search Report dated Mar. 12, 2020 for European Application No. 17837424.5, 15 pages.

Final Office Action mailed Apr. 24, 2014 for U.S. Appl. No. 13/514,331, 16 pages.

Final Office Action mailed Apr. 8, 2019 for U.S. Appl. No. 15/623,134, 13 pages.

Final Office Action mailed Aug. 31, 2017 for U.S. Appl. No. 14/777,511, 12 pages.

Final Office Action mailed Dec. 12, 2019 for U.S. Appl. No. 15/739,466, 9 pages.

Final Office Action mailed Dec. 20, 2017 for U.S. Appl. No. 14/777,505, 25 pages.

Final Office Action mailed Dec. 22, 2017 for U.S. Appl. No. 14/777,512, 13 pages.

Final Office Action mailed Feb. 21, 2017 for U.S. Appl. No. 13/882,013, 6 pages.

Final Office Action mailed Feb. 21, 2019 for U.S. Appl. No. 14/777,511, 18 pages.

Final Office Action mailed Feb. 27, 2018 for U.S. Appl. No. 14/777,504, 10 pages.

Final Office Action mailed Jan. 17, 2020 for U.S. Appl. No. 15/660,616, 14 pages.

Final Office Action mailed Mar. 13, 2017 for U.S. Appl. No. 15/163,890, 8 pages.

Final Office Action mailed Mar. 16, 2021 for U.S. Appl. No. 16/113,793, 11 pages.

Final Office Action mailed Mar. 18, 2021 for U.S. Appl. No. 15/660,616, 22 pages.

Final Office Action mailed Mar. 8, 2021 for U.S. Appl. No. 16/013,793, 16 pages.

Final Office Action mailed Nov. 17, 2017 for U.S. Appl. No. 14/777,507, 14 pages.

Final Rejection Office Action for U.S. Appl. No. 16/113,793 mailed on Nov. 8, 2022, 27 pages.

First Office Action dated Feb. 20, 2021 for Chinese Application No. 201780060346.2, with English language translation, 12 pages.

Fischer et al., "Ferro-microfluidic device for pathogen detection," IEEE Int Conf on Nano/Micro Eng and Molecular System China, 907-910 (2008).

Gijs, "Magnetic bead handling on-chip: new opportunities for analytical applications", Microfluid Nanofluid 1: 22-40 (2004).

Goldman et al., "Slow viscous motion of a sphere parallel to a plane wall-I motion through a quiescent fluid", Chem Eng Sci 22: 637-651 (1967).

Green, "The Sigma-Aldrich Handbook of Stains, Dyes & Indicators", Aldrich Chemical Co., Milwaukee, WI, 721-722 (1990).

Han et al., "Kynurenine aminotransferase and glutamine transaminase K of *Escherichia coli*: Identity with aspartate aminotransferase", Biochemical Journal 360(3): 617-623 (2001).

Horan et al., "Stable cell membrane labeling", Nature 340: 167-168 (1989).

Hughes, "Strategies for dielectrophoretic separation in laboratory-on-a-chip systems", Electrophoresis 23:2569-2582 (2002).

International Preliminary Report on Patentability for International Application No. PCT/US2021/041616 dated Jan. 26, 2023, 17 pages.

International Search Report and Written Opinion for International Application No. PCT/US2022/014987, mailed May 17, 2022, 19 pages.

International Search Report and Written Opinion mailed Aug. 11, 2014 for International Application No. PCT/US2014/030584, 7 pages.

International Search Report and Written Opinion mailed Aug. 20, 2014 for International Application No. PCT/US2014/030629, 9 pages.

International Search Report and Written Opinion mailed Aug. 5, 2014 for International Application No. PCT/US2014/028705, 6 pages.

International Search Report and Written Opinion mailed Aug. 5, 2014 for International Application No. PCT/US2014/029376, 9 pages.

International Search Report and Written Opinion mailed Dec. 1, 2022 for International Application No. PCT/US2021/041616, 22 pages.

International Search Report and Written Opinion mailed Dec. 23, 2016 for International Application No. PCT/US2016/039394, 8 pages.

(56) References Cited

OTHER PUBLICATIONS

International Search Report and Written Opinion mailed Feb. 22, 2018 for International Application No. PCT/US2017/065883, 13 pages.
International Search Report and Written Opinion mailed Feb. 8, 2011 for International Application No. PCT/US2010/059270, 10 pages.
International Search Report and Written Opinion mailed Oct. 10, 2014 for International Application No. PCT/US2014/029336, 12 pages.
International Search Report and Written Opinion mailed Oct. 18, 2011 for International Application No. PCT/US2011/039516, 7 pages.
International Search Report and Written Opinion mailed Oct. 6, 2017 for International Application No. PCT/US2017/043985, 9 pages.
International Search Report and Written Opinion mailed Sep. 13, 2016 for International Application No. PCT/US2016/040861, 6 pages.
Ise, "When, why, and how does like like like?—Electrostatic attraction between similarly charged species", Proc Jpn Acad B Phys Biol Sci 83:192-198 (2007).
Jayashree et al., "Identification and Characterization of Bile Salt Hydrolase Genes from the Genome of Lactobacillus fermentum MTCC 8711", Applied Biochemistry and Biotechnology 174(2): 855-866 (2014).
Kamei et al., "Microfluidic Genetic Analysis with an Integrated a-Si:H Detector", Biomed Microdevices 7: 147-152 (2005).
Kang et al., Monitoring of anticancer effect of cisplatin and 5-fluorouracil on HepG2 cells by quartz crystal microbalance and micro CCD camera:, Biosensors and Bioelectronics 26: 1576-1581 (2010).
Kashevsky, "Nonmagnetic particles in magnetic fluid: Reversal dynamics under rotating field", Phys Fluids 9: 1811-1818 (1997).
Kim et al., "Cloning and characterization of the bile salt hydrolase genes (bsh) from Bifidobacterium bifidum strains", Applied and Environmental Biology 70(9): 5603-5612 (2004).
Kim et al., "Synthesis of ferrofluid with magnetic nanoparticles by sonochemical method for MRI contrast agent", J Magn Magn Mater 289: 328-330 (2005).
Kose et al., "Ferrofluid mediated nanocytometry", Lab Chip 12: 190-196 (2012).
Kose et al., "Label-free cellular manipulation and sorting via biocompatible ferrofluids", Proc. Nat'l. Acad. Sci. USA, 106(51): 21478-21483 (2009).
Kose et al., "Towards Ferro-microfluidics for Effective and Rapid Cellular Manipulation and Sorting", Proceedings of the IEEE Int. Conf. on Nano/Microengineered and Molecular Systems, Jan. 6-9, 2008, pp. 903-906.
Kose et al., "Supporting information to Label-free cellular manipulation and sorting via biocompatible microfluids", Proceedings of the National Academy of Sciences USA; retrieved from the Internet: http://www.pnas.org/cgi/content/short/0912138106 (2009), 6 pages.
Kremser et al., "Capillary electrophoresis of biological particles: Viruses, bacteria, and eukaryotic cells", Electrophoresis 25: 2282-2291 (2004).
Kumar et al., "Molecular cloning, characterization and heterologous expression of bile salt hydrolase (bsh) from Lactobacillus fermentum NCD0394", Molecular Biology Reports 40(8): 5057-5066 (2013).
Lee et al., "Microelectromagnets for the control of magnetic nanoparticles", Appl Phys Lett 79: 3308-3310 (2001).
Lekka et al., "Elasticity of normal and cancerous human bladder cells studies by scanning force microscopy", Eur Biophys J 28: 312-316 (1999).
Liu et al., "Evidence for Localized Cell Heating Induced by Infrared Optical Tweezers", Biophys J 68: 2137-2144 (1995).
Maiorov, "Experimental Study of the Permeability of a ferrofluid in an alternating magnetic field", Magnetohydrodynamics 15: 135-139 (1979).
Mao et al., "Towards ferrofluidics for µ-TAS and lab on-a-chip applications", Nanotechnology 17: 34-47 (2006).
Massart, "Preparation of Aqueous Magnetic Liquids in Alkaline and Acid Media", IEEE Trans Magn 17: 1247-1248 (1981).
Menachery et al., "Controlling cell destruction using dielectrophoretic forces", NanoBiotechnology 152:145-149 (2005).
Muller et al., "The Potential of Dielectrophoresis for Single-Cell Experiments", IEEE Eng Biol Med Mag 22: 51-61 (2003).
Non-Final Office Action for U.S. Appl. No. 16/419,982, dated Nov. 22, 2022, 14 pages.
Non-Final Office Action for U.S. Appl. No. 17/704,820 mailed on Dec. 2, 2022, 10 pages.
Non-Final Office Action mailed Apr. 1, 2015 for U.S. Appl. No. 14/591,492, 7 pages.
Non-Final Office Action mailed Apr. 28, 2017 for U.S. Appl. No. 14/777,505, 24 pages.
Non-Final Office Action mailed Apr. 3, 2020 for U.S. Appl. No. 16/013,793, 18 pages.
Non-Final Office Action mailed Apr. 5, 2019 for U.S. Appl. No. 15/739,466, 8 pages.
Non-Final Office Action mailed Aug. 1, 2017 for U.S. Appl. No. 14/777,512, 18 pages.
Non-Final Office Action mailed Aug. 22, 2019 for U.S. Appl. No. 15/660,606, 10 pages.
Non-Final Office Action mailed Aug. 31, 2018 for U.S. Appl. No. 15/623,134, 12 pages.
Non-Final Office Action mailed Aug. 8, 2017 for U.S. Appl. No. 14/777,504, 11 pages.
Non-Final Office Action mailed Feb. 12, 2018 for U.S. Appl. No. 14/827,073, 25 pages.
Non-Final Office Action mailed Jan. 16, 2020 for U.S. Appl. No. 15/623,134, 10 pages.
Non-Final Office Action mailed Jan. 20, 2017 for U.S. Appl. No. 14/777,511, 13 pages.
Non-Final Office Action mailed Jan. 21, 2022 for U.S. Appl. No. 16/113,793, 17 pages.
Non-Final Office Action mailed Jan. 27, 2020 for U.S. Appl. No. 15/708,032, 10 pages.
Non-Final Office Action mailed Jan. 28, 2021 for U.S. Appl. No. 15/739,466, 9 pages.
Non-Final Office Action mailed Jul. 12, 2019 for U.S. Appl. No. 15/660,616, 17 pages.
Non-Final Office Action mailed Jul. 16, 2018 for U.S. Appl. No. 14/777,511, 14 pages.
Non-Final Office Action mailed Jul. 31, 2013 for U.S. Appl. No. 13/514,331, 11 pages.
Non-Final Office Action mailed Jul. 5, 2018 for U.S. Appl. No. 15/740,288, 12 pages.
Non-Final Office Action mailed Jun. 14, 2019 for U.S. Appl. No. 15/982,926, 19 pages.
Non-Final Office Action mailed Jun. 2, 2017 for U.S. Appl. No. 14/777,507, 10 pages.
Non-Final Office Action mailed Jun. 25, 2020 for U.S. Appl. No. 16/113,793, 8 pages.
Non-Final Office Action mailed Jun. 26, 2019 for U.S. Appl. No. 15/670,264, 11 pages.
Non-Final Office Action mailed Jun. 30, 2016 for U.S. Appl. No. 15/163,890, 8 pages.
Non-Final Office Action mailed Oct. 14, 2021 for U.S. Appl. No. 16/013,793, 8 pages.
Non-Final Office Action mailed Oct. 31, 2022 for U.S. Appl. No. 16/772,681, 22 pages.
Non-Final Office Action mailed Sep. 10, 2021 for U.S. Appl. No. 16/772,681, 20 pages.
Non-Final Office Action mailed Sep. 14, 2016 for U.S. Appl. No. 13/882,013, 5 pages.
Non-Final Office Action mailed Sep. 21, 2022 for U.S. Appl. No. 16/859,431, 14 pages.
Non-Final Office Action mailed Sep. 25, 2017 for U.S. Appl. No. 13/882,013, 6 pages.
Notice of Allowance for U.S. Appl. No. 16/859,431 dated Apr. 14, 2023, 9 pages.
Notice of Allowance for U.S. Appl. No. 16/859,431 mailed May 1, 2023, 02 pages.

(56) References Cited

OTHER PUBLICATIONS

Notice of Allowance for U.S. Appl. No. 17/704,820, dated May 2, 2023, 8 pages.
Office Action dated Feb. 21, 2022 for Canadian Application No. 2,902,324, 3 pages.
Office Action for Chinese Application No. CN201780097630, mailed on Mar. 31, 2022, 12 pages.
Office Action for Indian Application No. IN5808/DELNP/2012 mailed Jan. 24, 2023, 3 pages.
Pethig et al., "Applications of dielectrophoresis in biotechnology", Trends Biotechnol 15: 426-432 (1997).
Primiceri et al., "Cell chips as new tools for cell biology—results, perspectives and opportunities", Lab Chip 13: 3789-3802 (2013).
Romasi et al., "Development of Indole-3-Acetic Acid-Producing *Escherichia coli* by Functional Expression of IpdC, AspC, and Iad1," Journal of Microbiology and Biotechnology 23(12):1726-1736 (2013).
Sarsero et al., "A new family of integral membrane proteins involved in transport of aromatic amino acids in *Escherichia coli*", Journal of Bacteriology 173(10): 3231-3234 (1991).
Scherer et al., "Ferrofluids: Properties and Applications", Brazilian J Phys 45: 718-727 (2005).
Sebastian et al., "Formation of multilayer aggregates of mammalian cells by dielectrophoresis", J Micromech Microeng 16: 1769-1777 (2006).
Seltmann, A., et al., "Age-specific Gastrointestinal Parasite Shedding in Free-ranging Cheetahs (*Acinonyx jubatus*) on Namibian Farmland", Parasitology Research, Jan. 31, 2019, vol. 118(3), pp. 851-859.
Songbai. T. et al., "A digital quantification method for the detection of biomarkers on a microfluidic array chip", Sensors & Actuators: B. Chemical 298 (2019) 126851, 7 pages.
Steidler et al., "Genetically engineered Probiotics", Baillier's Best Practice and Research. Clinical Gastroenterology 17(5): 861-876 (2003).
Tung et al., "Magnetic properties of ultrafine cobalt ferrite particles", J Appl Phys 93: 7486-7488 (2003).
Wang et al., "Expression of rat pro cholecystokinin (CCK) in bacteria and in insect cells infected with recombinant Baculovirus", Peptides 18(9): 1295-1299 (1997).
Whelan et al., "A Transgenic Probiotic Secreting a Parasite Immunomodulator for Site-Directed Treatment of Gut Inflammation", Molecular Therapy 22(10): 1730-1740 (2014).
Yan et al., "Near-field-magnetic-tweezer manipulation of single DNA molecules", Phys Rev E 70: 011905 (2004), 5 pages.
Yellen et al., "Arranging matter by magnetic nanoparticle assemblers", Proc Natl Acad Sci USA 102: 8860-8864 (2005).
Zahn et al., "Ferrohydrodynamic pumping in spatially uniform sinusoidally time-varying magnetic fields", J of Magnetism and Magnetic Materials 149: 165-173 (1995).
Zhang et al., "A microfluidic system with surface modified piezoelectric sensor for trapping and detection of cancer cells", Biosens Bioelectron 26(2): 935-939 (2010).
Zhang et al., "Low temperature and glucose enhanced T7 RNA polymerase-based plasmid stability for increasing expression of glucagon-like peptide-2 in *Escherichia coli*", Protein Expression and Purification 29(1): 132-139 (2003).

* cited by examiner

SYSTEMS AND METHODS FOR BEAD-BASED ASSAYS IN FERROFLUIDS

RELATED APPLICATIONS

This application is a continuation of U.S. patent application Ser. No. 15/623,134, filed Jun. 14, 2017, and entitled "Systems and Methods for Bead-Based Assays in Ferrofluids", which is a divisional of U.S. application Ser. No. 14/777,512, filed Sep. 15, 2015, and entitled "Systems and Methods for Bead-Based Assays in Ferrofluids," which in turn is a national stage entry application of PCT Patent Application No. PCT/US2014/030584, filed Mar. 17, 2014, and entitled "Systems and Methods for Bead-Based Assays in Ferrofluids," which claims benefit under 35 USC 119 (e) of U.S. Provisional Patent Application No. 61/798,087, filed Mar. 15, 2013, and entitled, "Bead-Based Assays in Biocompatible Ferrofluids." The present application incorporates herein by reference each disclose of the above-referenced applications in its entirety.

FIELD OF THE DISCLOSURE

The present disclosure relates to extraction and/or separation of particles in ferrofluids.

BACKGROUND OF THE DISCLOSURE

In immuno-magnetic separation, magnetic micro-beads covered with specific ligands are introduced into a complex biological sample to tag target particles in a mix (e.g., molecules, proteins, cells or other biological entities). Using an external magnetic field gradient, the tagged entities may be separated (e.g., focused, concentrated, precipitated), then extracted and purified for subsequent processing. These beads may also be used directly in biological assays (e.g., ELISA, PCR, gene sequencing, etc.) as they carry their target load to a sensor or a bio-functional surface.

A limitation of some magnetic bead separation systems is the wide distribution of the amount of magnetic content in each bead. This may be the case even for beads from the very same batch, and is a direct consequence of practicality in existing manufacturing methods. As a result, it may be impractical to attempt to distinguish bead tags based on the magnitude of the forces experienced by the magnetic beads from magnetic field, unless there is a considerable size difference between them (e.g., 1 micron vs. 10 micron beads).

SUMMARY OF THE DISCLOSURE

The teachings of this disclosure are a further application and development of a previous series of disclosures, including, for example PCT publication no. WO2011/071912 and WO2012/057878, the noted disclosures of which are all herein incorporated by reference in their entireties.

In some embodiments of the present disclosure, methods for extracting a target molecule from a mix of molecules are provided. Such methods may include suspending a plurality of non-magnetic beads in a ferrofluid, the non-magnetic beads being functionalized with at least one predetermined first molecule configured to bind with a target particle, and mixing or otherwise exposing the ferrofluid to a plurality of particles forming a mix, where target particles contained in the plurality of particles link with the first molecules functionalized on the non-magnetic particles. Such methods may further include flowing the mix through at least one microfluidic channel, applying a magnetic field to at least a portion of the at least one channel, where the magnetic field is configured to exert an indirect force on the non-magnetic beads to separate the non-magnetic beads from the ferrofluid, and extracting and/or otherwise separating the non-magnetic beads from the mix, wherein, as a result of the extraction, the target particles contained in the plurality of particles are separated from the mix.

Some embodiments provide a system for extracting a target molecule from a mix of molecules, and may comprise a plurality of non-magnetic beads suspended in a ferrofluid, the non-magnetic beads being functionalized with at least one predetermined first molecule configured to bind with a target particle, a plurality of particles, wherein the plurality of particles are mixed with the ferrofluid containing the non-magnetic beads resulting in a ferrofluid mix, and a microfluidic device comprising at least one microfluidic channel, where the device may be configured to dynamically and/or statically receive an amount of the mix. The magnetic field means may be configured to apply a magnetic field to at least a portion of the at least one channel to exert an indirect force on the non-magnetic beads in the ferrofluid mix, and separate the non-magnetic beads from the ferrofluid. The system may further include at least one outlet in communication with the at least one microfluidic channel, the at least one outlet configured to receive and extract the separated non-magnetic beads from the ferrofluid.

Some embodiments may further include one and/or another of the following additional features:

- the first molecule comprises a ligand;
- the target particle comprises a biological particle, where the biological particle may comprise at least one of an organic molecule, of a cell, a bacteria, a virus, DNA, RNA, a carbohydrate, a protein, a biomarker, a hormone, kinase, enzyme, cytokine, toxin, and any fragments thereof;
- the magnetic field source includes at least one of planar electrodes, electromagnets or a magnet array;
- detecting the target particles after at least one of separation and extraction via detection means, where the detecting comprises a flow cytometer and/or the like;
- the detection means includes any of an optical scanner/detector, and/or other detecting means, optical or otherwise, familiar to those of skill in the art, including, for example those found in any one and/or another of U.S. Pat. No. 4,448,534, WO2013/155525, WO2008/042003, U.S. Pat. No. 8,364,409, WO1991/001381, and WO2013/054311;
- the ferrofluid includes a plurality of magnetic nanoparticles and the magnetic field is configured to drive the magnetic nanoparticles in a first direction opposite a direction in which the non-magnetic beads are driven; and
- the separated non-magnetic beads flow into at least one outlet port in communication with the at least one microfluidic channel, such that the non-magnetic beads may be extracted or otherwise collected therefrom.

The above-noted embodiments, as well as other embodiments, will become even more evident with reference to the following detailed description and associated drawing, a brief description of which is provided below.

DETAILED DESCRIPTION OF SOME OF THE EMBODIMENTS

Magnetic bead based approaches have positively impacted the speed, throughput and simplicity of biological assays and protocols. Instead of using a standard buffer with magnetic microbeads to extract and work with target entities, embodiments of the present disclosure present systems and methods using non-magnetic functionalized beads suspended in a ferrofluid (e.g., a biocompatible ferrofluid). Since non-magnetic items placed in a ferrofluid medium feel repulsive forces (i.e., an indirect force) in the presence of externally applied magnetic field gradients, they can be used to capture, enrich, collect and detect molecular and cellular entities (i.e., at least biological entities) within biocompatible ferrofluids. This is a direct extension of earlier systems and methods disclosed in WO2011/071912 and WO2012/057878, where cells can be any one or more of manipulated, captured, detected and quantified in a ferrofluid without any labels. While micro-sized cells can be generally be manipulated in a label-free fashion inside ferrofluids without the need for any labels, smaller biological particles like viruses, DNA, RNA, proteins and other biological molecules may be too small to respond to the indirect/repulsive magnetic forces in ferrofluids within reasonable times. Thus, in some embodiments, using bead-based assays as opposed to label-free approaches extends the high utility of ferrofluid concentration/separation systems/methods from strictly cell assays to other molecular assays as well.

Thus, in some embodiments, instead of using magnetic beads in a standard, clear biological buffer, some embodiments of the present disclosure use non-magnetic beads in a ferrofluid to run bead-based extraction, purification and/or ultimate detection of target moieties. Thus, in some embodiments, it becomes possible to conduct virtually all biological assays in ferrofluids. Aside from being the dual opposite of immuno-magnetic assays, embodiments of the present disclosure are also different in at least several aspects. First, the magnetic force on the beads suspended in ferrofluid is repulsive/indirect (as opposed to attractive as in standard immuno-magnetic methods). The repulsive force enables much better localization, manipulation and/or focusing of the non-magnetic beads towards, for example, a bio-functional surface, thereby inherently increasing the sensitivity of a bead-based assay. Second, while bead manufacturing technology enables high precision bead diameters, there is typically much less control on the volume of the magnetic phase integrated inside a magnetic bead. As a result, magnetic forces acting on tagging beads is much more uniform in bead-based assays conducted in ferrofluids, enabling, in some embodiments, higher precision, repeatability, and reliability in final results.

Figure 1:
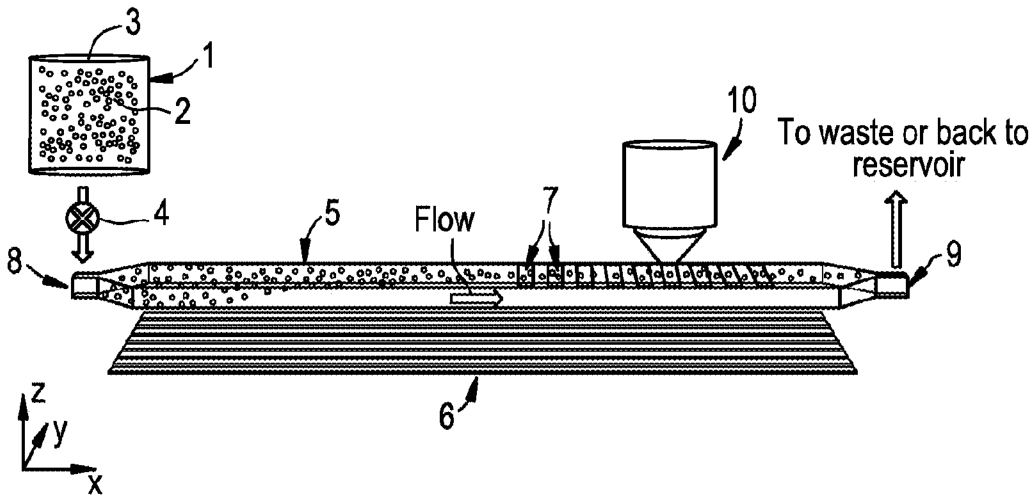
FIG. 1 is a schematic of a bead-based assay for a ferrofluid, according to some embodiments of the present disclosure.

FIG. 1 illustrates a bead-based assay utilizing a ferrofluid according to some embodiments. As shown, an initial sample containing a mixture of particles (e.g., moieties 2, including target moieties) and functionalized beads is mixed with a biocompatible ferrofluid 3 in a reservoir 1. After an incubation period in which target moieties bind with the molecules functionalized onto the beads, an external force, such as a pressure source, e.g., a pump 4, introduces the overall mixture into a channel inlet 8 that is connected to fluidic channel 5 that sits atop a magnetic field source 6. The magnetic field source 6, which is configured to apply a force, either directly or indirectly to particles/beads of the mix (e.g., on non-magnetic particles/beads), such that the functionalized beads are forced upward and focused. The magnetic source may comprise at least one of a planar electrode(s), an electromagnet(s) and a permanent magnet(s), each of which may be arranged in an array. In some embodiments, the beads (along with target particles/moieties bound to the functionalized molecules), move along the channel ceiling (e.g., roll) and interact serially with receptor regions 7 on that surface. Specific interactions between the particles 2 on the surface of the beads and the receptor regions 7 result in the temporary, and in some embodiments permanent, capture of beads. In some embodiments, detecting means, such as an optical scanner 10, may be provided and configured to detect the target particles captured and/or moving along the receptor regions 7. The mixture flows through to the channel outlet 9, in some embodiments, to waste or back to the reservoir 1.

Figure 2:
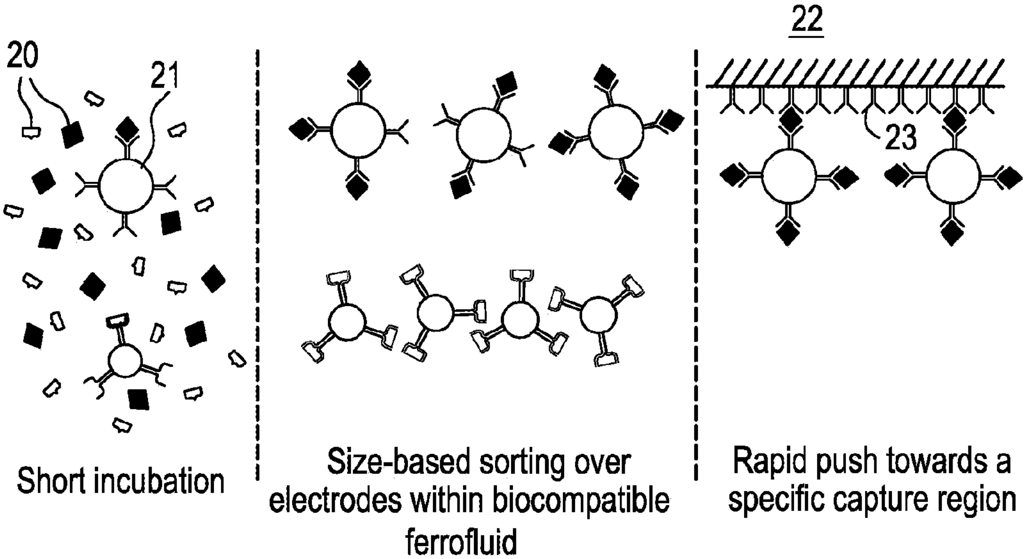
FIG. 2 shows a bead-based bioassay in a ferrofluid according to some embodiments of the present disclosure.

FIG. 2 illustrates some embodiments, where a simple bead-based bioassay in a biocompatible ferrofluid is presented. Initially, the complex sample is incubated with bead tags 21, which are then sorted inside a bio-ferrofluidic device based on size. A plurality of non-magnetic beads 21 with at least one predetermined first molecule, in one embodiment, a ligand, binds with target particles 20 in the ferrofluid. Applying magnetic field gradients from below, the bead tags 21 are rapidly pushed and concentrated towards a corresponding capture surface 22. The capture surface 22, in one embodiment, includes receptors 23 to capture the target particles 20. The main role of the ferrofluid here is to accelerate mass manipulation and transport toward surfaces.

When using non-magnetic beads in ferrofluids, the force on each bead is proportional to the volume of ferrofluid that they displace. Hence, bead populations with limited size distributions may be easily distinguished from each other. For example, beads above about 1 micrometer in diameter may be easily separated and sorted from each other based on a size difference of just 1 micron (PNAS 106 (51), p 21478, 2009). Hence bead populations of various sizes may be used to multiplex bio-assays without the need to use any chromophores.

Accordingly, in some embodiments, the ability to push/force (either directly or indirectly) the beads instead of attracting (i.e., pulling) them may allow the user to:

- selectively focus, separate, sort, concentrate and/or capture them; and
- count the beads (e.g., one at a time), as they pass through a detection region (e.g., flow cytometry), which, in some embodiments, may obviate the need to use hydrodynamic focusing in such applications.

In some embodiments, one can use a combination of magnetic and non-magnetic beads to increase separation efficiency in an assay. Accordingly, using a ferrofluid medium, magnetic beads may be configured such that they could be manipulated in the opposite direction of non-magnetic beads/particles.

Thus, in some embodiments, bead-based assays in ferrofluids can be used to quantify concentrations of any of proteins, molecular biomarkers, hormones, kinases, enzymes, cytokines, toxins, viruses and DNA/RNA fragments. Moreover, systems according to some embodiments may also be used as an enrichment step prior to traditional techniques, such as culture, ELISA, and PCR.

In some embodiments, captured beads and entities can be released and collected at an outlet port by destabilizing the colloidal suspension of the ferrofluid (via changes in pH and/or salt or other additives).

Some embodiments of this disclosure may be used, for example, simultaneously with label-free assays in the same ferrofluid. In such a combined approach, cellular assays may be run simultaneously with biomolecular assays. Some embodiments may also be used as a pathogen detection panel and configured for detecting and/or quantifying bacterial pathogens in a label-free fashion while detecting viruses or other smaller antigens using non-magnetic beads as labels.

Some embodiments of this disclosure may be used, for example, in the context of drug discovery. In such approaches, bead-based assays may be used to at least one of detect, identify and quantify binding between a candidate drug molecule and a number of ligand targets.

Any and all references to publications or other documents, including but not limited to, patents, patent applications, articles, webpages, books, etc., presented in the present application, are herein incorporated by reference in their entirety.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements corresponding to bead assays. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Correspondingly, some embodiments of the present disclosure may be patentably distinct from one and/or another reference by specifically lacking one or more elements/features. In other words, claims to certain embodiments may contain negative limitation to specifically exclude one or more elements/features resulting in embodiments which are patentably distinct from the prior art which include such features/elements.

What is currently claimed is:

1. A method for extracting a target particle from a mix of particles, comprising:
- suspending a plurality of non-magnetic beads in a ferrofluid; the non-magnetic beads being functionalized with at least one predetermined first molecule configured to bind with a target particle;
- mixing or otherwise exposing the ferrofluid to a plurality of particles forming a mix, wherein one or more target particles of the plurality of particles bind with at least some of the non-magnetic beads;
- flowing the mix through at least one microfluidic channel; and
- applying a magnetic field to at least a portion of the at least one channel, wherein the magnetic field is configured to exert an indirect force on the non-magnetic beads to separate the non-magnetic beads from the ferrofluid, and
- flowing the separated non-magnetic beads over at least one receptor region provided along the channel, wherein the target particles bind to the molecules of the receptor region.

2. The method of claim 1, further comprising extracting the non-magnetic beads from the mix.

3. The method of claim 1, further comprising detecting the target particles after at least one of separation and extraction via detection means.

4. A method for assaying a target particle, comprising:
- suspending a plurality of non-magnetic beads in a ferrofluid;
- mixing or otherwise exposing the ferrofluid to a plurality of particles forming a mix, the plurality of particles including one or more target particles;
- flowing the mix such that the ferrofluid carries the non-magnetic beads; and
- capturing the one or more target particles.

5. A bead-based assay ferrofluid apparatus comprising:
- a ferrofluid including a sample containing a mixture of particles and functionalized beads;
- a pump;
- a channel inlet;
- a fluidic channel; and
- a magnetic field source comprising at least one of one or more planar electrodes, an electromagnet and a permanent magnet.

6. The apparatus of claim 5, further comprising a receptor region.

7. The apparatus of claim 5, further comprising a detection means.

8. The method of claim 5, wherein capturing the one or more target particles is via a receptor region.

9. A system for extracting a target molecule from a mix of molecules, comprising:
- a plurality of non-magnetic beads suspended in a ferrofluid, the non-magnetic beads being functionalized with at least one predetermined first molecule configured to bind with a target particle;
- a plurality of particles, wherein the plurality of particles arc mixed with the ferrofluid containing the non-magnetic beads resulting in a ferrofluid mix; and
- a microfluidic device comprising at least one microfluidic channel, the device configured to dynamically and/or statically receive an amount of the mix;
- magnetic field means configured to:
  - apply a magnetic field to at least a portion of the at least one channel to exert an indirect force on the non-magnetic beads in the ferrofluid mix,
  - separate the non-magnetic beads from the ferrofluid, and
  - direct the non-magnetic beads to at least one receptor region.

10. The system of claim 9, further comprising at least one outlet.

11. The system of claim 9, wherein the magnetic field source includes at least one of planar electrodes, electromagnets or a magnet array.

12. The method of claim 1, wherein the ferrofluid includes a plurality of magnetic nanoparticles and the magnetic field is further configured to drive the magnetic nanoparticles in a first direction opposite a second direction in which the non-magnetic beads are driven.

* * * * *